(12) United States Patent
Vollmann

(10) Patent No.: US 10,537,411 B2
(45) Date of Patent: Jan. 21, 2020

(54) METHOD TO PRODUCE A MONOLITHIC FORM BODY

(71) Applicant: DENTSPLY SIRONA Inc., York, PA (US)

(72) Inventor: Markus Vollmann, Gelnhausen (DE)

(73) Assignee: DENTSPLY SIRONA Inc., York, PA (US)

( * ) Notice: Subject to any disclaimer, the term of this patent is extended or adjusted under 35 U.S.C. 154(b) by 298 days.

(21) Appl. No.: 15/453,610

(22) Filed: Mar. 8, 2017

(65) Prior Publication Data
US 2018/0256297 A1  Sep. 13, 2018

(51) Int. Cl.
| *A61C 13/00* | (2006.01) |
| *A61C 5/77* | (2017.01) |
| *A61C 8/00* | (2006.01) |
| *C03C 23/00* | (2006.01) |

(52) U.S. Cl.
CPC .......... *A61C 13/0018* (2013.01); *A61C 5/77* (2017.02); *A61C 8/0001* (2013.01); *A61C 13/0022* (2013.01); *A61C 13/0024* (2013.01); *C03C 23/001* (2013.01)

(58) Field of Classification Search
None
See application file for complete search history.

(56) References Cited

U.S. PATENT DOCUMENTS

| 4,515,634 A * | 5/1985 | Wu ..................... C03C 4/0021 106/35 |
| 5,391,522 A * | 2/1995 | Goto ..................... C03C 10/00 501/4 |
| 5,702,514 A * | 12/1997 | Petticrew ............... A61C 13/20 106/35 |
| 5,744,208 A * | 4/1998 | Beall ..................... C03C 3/087 428/64.1 |
| 6,555,175 B2 * | 4/2003 | Johnson ................. C08J 7/12 427/393.5 |
| 6,586,038 B1 * | 7/2003 | Chabrecek ............. C08J 7/12 351/159.33 |
| 6,818,573 B2 * | 11/2004 | Petticrew ............... A61C 13/20 106/35 |
| 2003/0143335 A1 * | 7/2003 | Qiu ..................... A61L 27/34 427/430.1 |
| 2003/0215770 A1 * | 11/2003 | Sekino ................ A61C 13/083 433/218 |
| 2004/0024388 A1 * | 2/2004 | Altshuler ............. A61C 1/0046 606/2 |
| 2009/0246253 A1 * | 10/2009 | Ding ..................... A61L 31/10 424/426 |

(Continued)

FOREIGN PATENT DOCUMENTS

| DE | 19750794 A1 | 6/1999 |
| DE | 10336913 A1 | 3/2005 |

(Continued)

*Primary Examiner* — Cachet I Proctor
(74) *Attorney, Agent, or Firm* — Dentsply Sirona Inc.

(57) ABSTRACT

The invention relates to a method for producing a monolithic form body, in particular a dental restoration, comprising the steps of: providing of a blank, producing of the form body through pressing and/or machining of the blank, and softening of the form body exclusively in its surface region by irradiation with infrared radiation.

17 Claims, 1 Drawing Sheet

(56) References Cited

U.S. PATENT DOCUMENTS

| | | | | |
|---|---|---|---|---|
| 2010/0303722 | A1* | 12/2010 | Jin | A61L 27/30 424/9.1 |
| 2012/0015138 | A1* | 1/2012 | Chehimi | C08F 2/50 428/95 |
| 2012/0094822 | A1* | 4/2012 | Castillo | A61K 6/0094 501/59 |
| 2012/0129131 | A1* | 5/2012 | Baehre | A61B 17/00491 433/173 |
| 2012/0237745 | A1* | 9/2012 | Dierkes | A61K 6/0215 428/215 |
| 2013/0059272 | A1* | 3/2013 | Jahns | A61K 6/0276 433/199.1 |
| 2014/0135202 | A1* | 5/2014 | Ritzberger | C03C 3/083 501/32 |
| 2014/0148328 | A1* | 5/2014 | Castillo | A61K 6/0273 501/2 |
| 2015/0104655 | A1* | 4/2015 | Kim | C03B 11/08 428/432 |
| 2016/0060159 | A1* | 3/2016 | Kim | C03C 10/0027 501/32 |

FOREIGN PATENT DOCUMENTS

| | | |
|---|---|---|
| DE | 102009060274 A1 | 6/2011 |
| DE | 102015108171 A1 | 11/2016 |
| EP | 0231773 | 8/1987 |
| EP | 1484031 B1 | 8/2007 |
| EP | 2662342 A1 | 11/2013 |
| WO | 2012175450 A1 | 12/2012 |
| WO | 2012175615 A1 | 12/2012 |
| WO | 2013053865 A2 | 4/2013 |

* cited by examiner

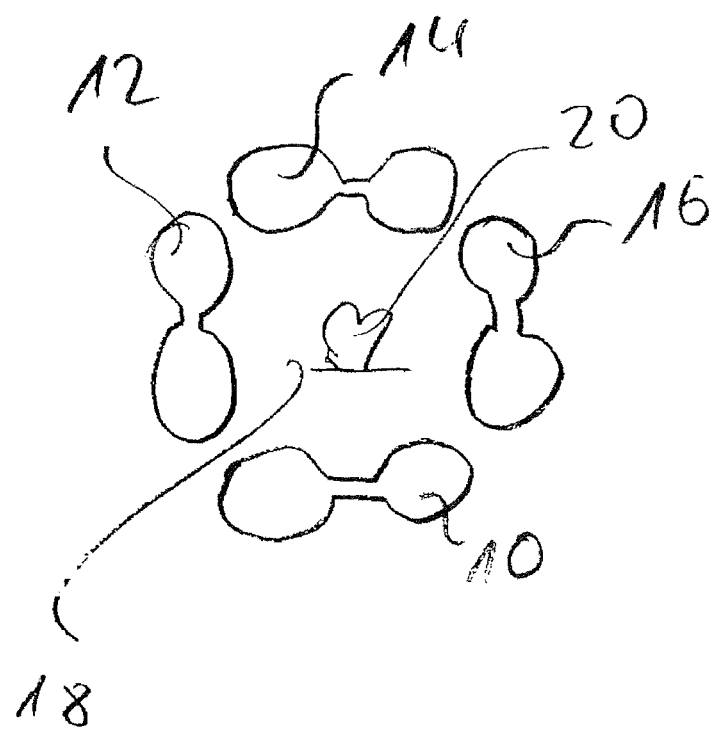

METHOD TO PRODUCE A MONOLITHIC FORM BODY

TECHNICAL FIELD

The invention relates to a method for producing a monolithic form body, in particular a dental restoration, such as a bridge, crown, coping, inlay, onlay or veneer, of lithium silicate glass ceramic.

BACKGROUND

The use of lithium silicate glass ceramic has proven itself in the field of dental technology because of its strength and biocompatibility. The strength can additionally be increased by adding a stabilizer from the group consisting of zirconium oxide, hafnium oxide, or mixtures thereof, to the starting raw materials (DE 10 2009 060 274 A1, WO 2012/175450 A1, WO 2012/175615 A1, WO 2013/053865 A2, EP 2 662 342 A1).

Lithium silicate glass ceramic materials, in particular if a blank contains lithium metasilicate as the main crystal phase, enable problem-free machining without high tool wear. To increase the strength, the lithium metasilicate is at least partially converted into lithium disilicate by subsequent heat treatment (DE 197 50 794 A1, DE 103 36 913 B4).

To produce dental restorations, it is known to press plastified ceramic material into a mold cavity present in a curable investment material (EP 1 484 031 B1, EP 0 231 773 A1).

DE 10 2010 108 171 A1 discloses a method to increase the strength of a form body consisting of lithium silicate glass ceramic. Lithium ions are replaced by alkali metal ions of greater diameter to generate a surface compressive stress.

SUMMARY OF THE INVENTION

The present invention seeks to improve upon prior method for the production of a monolithic form body (20), in particular a dental restoration such as a crown, bridge, coping, inlay, onlay or veneer, of lithium silicate glass ceramic, comprising the steps of: providing a blank; producing the form body by pressing and/or machining the blank; and softening of the form body exclusively in the surface region by irradiating the form body with infrared radiation.

In yet another aspect, any of the aspects of the present invention may be further characterized by one or any combination of the following features: the form body (20) is softened to a depth T of T≤100 µm, preferably T≤50 µm, in particular T≤10 µm; the form body (20) is irradiated with an infrared radiation whose main radiation components lie in the wavelength range between 2.7 µm and 4.7 µm, in particular between 35% and 50%; a blank of lithium silicate glass ceramic is used which contains lithium disilicate as the main crystal phase; the form body (20) is heat-treated after its production for the formation of metasilicate and/or disilicate crystals, in particular disilicate crystals, as the main crystal phase; a form body (20) of lithium silicate glass ceramic is used, the glass content of which is in a ratio of 20:65 to the crystal component in percentage by volume, preferably 40:50, in particular 45:55, in particular the glass content is equal to that of the crystal component or crystal components; crystal/crystallite size is ≤2 µm; the form body (20) is a dental restoration, which is removed from the mouth of a patient, grinded and then irradiated with infrared radiation and finally reinserted; the form body (20) is irradiated with the infrared radiation over a time t where 10 seconds≤t≤150 seconds, in particular 30 seconds≤t≤120 seconds; the lithium silicate glass ceramic in its starting composition, contains or consists of the following in percentage by weight:

| | |
|---|---|
| $SiO_2$ | 54.0-62.0, preferably 57.0-62.0 |
| Nucleating agents, such as $P_2O_5$ | 5.0-6.0 |
| $Al_2O_3$ | 1.5-3.5 |
| $Li_2O$ | 13.0-16.0 |
| $K_2O$ | 0.6-1.8 |
| $ZrO_2$ | 8.0-11.5 |
| $B_2O_3$ | 0-6.0 |
| $Na_2O$ | 0-1.9 |
| Color pigments | 0-8.0 | such as $MnO$, $Fe_2O_3$, $Tb_2O_3$, $Er_2O_3$, $Pr_2O_3$, $CeO_2$, $Y_2O_3$, $V_2O_3$;

the lithium silicate glass ceramic in its starting composition, contains or consists of the following in percentage by weight:

| | |
|---|---|
| $SiO_2$ | 57.0-60.0 |
| Nucleating agents such as $P_2O_5$ | 5.2-5.6 |
| $Al_2O_3$ | 2.6-3.2 |
| $Li_2O$ | 13.5-15.0 |
| $K_2O$ | 0.8-1.4 |
| $ZrO_2$ | 9.0-11.0 |
| $B_2O_3$ | 0-5.0 |
| $Na_2O$ | 0-1.5 |
| Color pigments | 2-7.0 | wherein $CeO_2$ may also be contained;
the lithium silicate glass ceramic is derived from the following starting components:

| | |
|---|---|
| $SiO_2$ | 58 |
| $P_2O_5$ | 5 |
| $Al_2O_3$ | 3 |
| $Li_2O$ | 15 |
| $K_2O$ | 1 |
| $ZrO_2$ | 10.0 |
| Color pigment(s) | 4 | such as $MnO$, $Fe_2O_3$, $Tb_2O_3$, $Er_2O_3$, $Pr_2O_3$, $Y_2O_3$, $V_2O_3$
Additives (refining agent and nucleating agent) 4
such as $B_2O_3$, $CeO_2$, $Na_2O$;
the form body (20) is covered, at least in sections, with a paste including alkali metal ions of greater diameter than lithium ions before subjected to its infrared irradiation; the form body (20) is coated with a viscous solution or dispersion of a salt including an alkali metal ion as the paste; the paste is applied to the form body (20) by spraying; to derive the paste the salt is mixed with at least one substance from the group consisting of 1,4-butanediol, hexanetriol, or a mixture of the two substances; the paste is preferably applied to all the surfaces of the form body, in particular with a thickness D of about 0.5 mm or less, in particular of 0.1 mm<D<0.4 mm; or any combination thereof.

It should be appreciated that the above referenced aspects and examples are non-limiting as others exist with the present invention, as shown and described herein. For example, any of the above-mentioned aspects or features of the invention may be combined to form other unique configurations, as described herein, demonstrated in the drawings, or otherwise.

BRIEF DESCRIPTION OF THE DRAWINGS

FIG. 1 shows a process according to the present invention.

DETAILED DESCRIPTION OF THE INVENTION

The object of the present invention is to further develop a method of the type mentioned at the start in such a way that cracks and other surface defects that are seen during working, such as grinding, of the form body, are remedied. At the same time, a desired gloss effect is to be achieved if desired.

To solve this problem, the invention essentially provides the following:
  providing of a blank
  producing the form body by pressing and/or machining the blank
  softening of the form body exclusively in its surface region by irradiating the form body with infrared radiation.

The form body should thereby be softened to a depth of $T \leq 100$ μm, preferably $T \leq 50$ μm, in particular $T \leq 10$ μm.

Furthermore, the glass content of the lithium silicate glass ceramic should lie between 20% by volume and 60% by volume, in particular between 40 and 60% by volume. It is preferably provided that the ratio of the glass content to the crystal content is 45:55 percent by volume, in particular approximately 50:50 percent by volume.

The main crystal phase of the form body should be lithium disilicate. It is preferably provided that the size of the crystals or crystallites of the lithium silicate glass ceramic is below 2 μm. The composition should also be selected such that the $T_G$ (glass transition) temperature is <800° C.

In accordance with the invention, surface defects are remedied through the fact that the form body is softened exclusively on the surface, as a result of which, in particular, cracks are repaired. At the same time a gloss effect results due to the melting.

Since melting is confined to the surface, the form body retains its shape. In other words, the form body is heated in a short time in such a way that there is surface melting, i.e., temperatures occur which would lead to a deformation if a volume heating would take place.

Volume heating for ceramic materials is already known, for instance from DE 26 56 288 A1. In this process, a veneer ceramic is heated up to the full depth when it is applied to a metal or crown framework, to obtain a void-free veneering layer. At the same time, adhesion between metal and ceramic is to be improved. For volume heating, short-wave infrared radiation in the range between 0.7 and 1.5 μm is used.

To preclude unwanted volume heating, it is provided, in particular, for the surface heating to be carried out with an infrared radiation whose main radiation content is in the wavelength range between 2.7 μm and 4.7 μm, the main radiation content being in particular between 35% and 50%.

The irradiation time should be between 10 and 150 seconds, in particular between 30 and 120 seconds.

The blank itself can already consist of lithium silicate glass ceramic. There is naturally also the possibility that, after the form body has been produced, it is still subjected to heat treatments in the customary manner to form metasilicate and/or disilicate crystals, in which case the disilicate crystals are present as the main crystal phase, especially after completion of the heat treatments.

If surface defects are to be healed in accordance with the prior art, a so-called healing fire conventional treatment can be carried out, i.e., an additional glaze is applied to the glass ceramic, which is then subjected to a heat treatment of approx. 12 minutes (time required for heating, holding and cooling).

On the other hand, due to the short exposure to radiation, the surface can be smoothed to a gloss very rapidly, without the radiation penetrating deeply. The dental restoration can be removed in the dental practice (chairside) for any grinding procedure that may be necessary for the correct fitting of the dental restoration to the residual teeth, the dental restoration is then reinserted after the short infrared irradiation according to the invention and cooling to body temperature.

This is preceded by etching of the inner surface of the dental restoration to insure adhesion to a preparation.

With regard to the blank, it should be noted that a blank is also to be understood as a pellet made of compacted powdery material which is used with known muffle systems to press a dental restoration.

Alternatively, the blank can be machined through the usual methods such as milling and grinding to provide the desired form body, in particular dental restoration. After processing, a healing on the surface and a smoothing to the gloss then take place within a very short time.

According to a further inventive proposal, the form body is covered, at least in sections, with a paste containing alkali metal ions of greater diameter than lithium ions before the infrared radiation. Thus, an ion exchange can take place during the infrared irradiation, so that not only is a smoothing/brightening or a gloss development brought about by the infrared radiation, but at the same time lithium ions are replaced by alkali metal ions of greater diameter so that a surface compressive stress and thus a strength increase is achievable.

In particular, provision is made for the form body to be coated with a viscous solution or dispersion of an alkali metal salt as the paste. Application through spraying or spreading is also possible.

The thickness of the paste should be at about 0.5 mm or less. It must be insured that infrared radiation can penetrate into the surface of the form body to a sufficient extent so that it can be absorbed and thus the form body can be heated on its surface to the required extent.

In particular, the invention is distinguished by the fact that the lithium silicate glass ceramic contains, in percentage by weight, in its starting composition:

| | |
|---|---|
| $SiO_2$ | 54.0-62.0, preferably 57.0-62.0 |
| Nucleating agent, such as $P_2O_5$ | 5.0-6.0 |
| $Al_2O_3$ | 1.5-3.5 |
| $Li_2O$ | 13.0-16.0 |
| $K_2O$ | 0.6-1.8 |
| $ZrO_2$ | 8.0-11.5 |
| $B_2O_3$ | 0-6.0 |
| $Na_2O$ | 0-1.9 |
| Color pigments such as $MnO$, $Fe_2O_3$, $Tb_2O_3$, $Er_2O_3$, $Pr_2O_3$, $CeO_2$, $Y_2O_3$, $V_2O_3$ | 0-8.0 |

The lithium silicate glass ceramic of the following starting composition in percentage by weight is preferred:

| | |
|---|---|
| $SiO_2$ | 57.0-60.0 |
| Nucleating agent, such as $P_2O_5$ | 5.2-5.6 |
| $Al_2O_3$ | 2.6-3.2 |
| $Li_2O$ | 13.5-15.0 |
| $K_2O$ | 0.8-1.4 |
| $ZrO_2$ | 9.0-11.0 |

-continued

| | |
|---|---|
| $B_2O_3$ | 0-5.0 |
| $Na_2O$ | 0-1.5 |
| Color pigments ($CeO_2$ may also be used as a color pigment) | 2-7.0 |

The lithium silicate glass ceramic of the following starting components in percentage by weight is especially preferred:

| | |
|---|---|
| $SiO_2$ | 58 |
| $P_2O_5$ | 5 |
| $Al_2O_3$ | 3 |
| $Li_2O$ | 15 |
| $K_2O$ | 1 |
| $ZrO_2$ | 10.0 |
| Color pigment(s) such as MnO, $Fe_2O_3$, $Tb_2O_3$, $Er_2O_3$, $Pr_2O_3$, $Y_2O_3$, $V_2O_3$ | 4 |
| Additives such as $Na_2O$, nucleating agent, such as $B_2O_3$ or refining agent such as $CeO_2$ | 4 |

In an embodiment, the invention is characterized in that the blank or the form body is subjected at least to a first heat treatment W1 at a temperature $T_{W1}$ over a period $t_{W1}$, wherein 620° C.$\leq T_{W1} \leq$800° C., in particular 650° C.$\leq T_{W1} \leq$750° C., and/or 1 minute$\leq t_{W1} \leq$200 minutes, preferably 10 minute$\leq$W1$\leq$60 minutes. If the blank is heat-treated, the form body is then produced therefrom.

A corresponding lithium silicate glass ceramic blank can be worked without difficulty, with minimal tool wear. A corresponding blank can also be pressed into a desired geometry.

In particular, in order to achieve a final crystallization, the lithium silicate glass ceramic blank, or the form body, is subjected to a second heat treatment W2 at a temperature $T_{W2}$ for a time $t_{W2}$ after the first heat treatment W1, wherein 800° C.$\leq T_{W2} \leq$1040° C., 800° C.$\leq T_{W2} \leq$900° C. and/or 2 minutes$\leq t_{W2} \leq$200 minutes, preferably 3 minutes$\leq t_{W2} \leq$30 minutes.

The following temperature values and heating rates are preferably selected in the heat treatment steps leading to a pre-crystallization or final crystallization. With respect to the first heat treatment W1, it is provided in particular that this takes place in two stages, with a first holding stage in the range between 640° C. and 680° C. and a second holding stage between 720° C. and 780° C. In each stage, the heated blank is held for a period of time, preferably between 35 and 45 minutes in the first stage and preferably between 15 and 25 minutes in the second stage.

The form body is preferably covered, at least over regions, with a paste containing potassium ions, in particular with a paste containing $KNO_3$, KCl or $K_2CO_3$, or with a paste containing sodium ions, in particular with a paste containing $NaNO_3$, sodium acetate or sodium salts of organic acids, or with a paste containing a mixture of potassium ions and sodium ions, in particular in the ratio 50:50 mol. %, preferably with a paste containing $NaNO_3$ and $KNO_3$.

Further details, advantages and features of the invention result not only from the claims, the characteristics to be drawn from them—both on their own and/or in combination—but also from the following description of preferred embodiments.

For the production of blanks, the required raw materials were first melted over a period of more than two hours at 1540° C. According to the manufacturer, the following starting composition was used in percentage by weight to prepare lithium silicate glass and from this lithium silicate glass ceramic.

| | |
|---|---|
| $SiO_2$ | 58.1-59.1 |
| $P_2O_5$ | 5.8-5.9 |
| $Al_2O_3$ | 1.9-2.0 |
| $Li_2O$ | 18.5-18.8 |
| $K_2O$ | 1.9-2.0 |
| $ZrO_2$ | 9.5-10.5 |
| $CeO_2$ | 1.0-2.0 |
| $Tb_4O_7$ | 1.0-1.5 |
| $Na_2O$ | 0-0.2 |

The melt was then filled into containers, the filling temperature of the melt being 1360° C. The temperature within the containers was approximately in the range 800° C. to 1250° C. The melt was then cooled to 300° C. to 500° C. in the containers. Subsequently, a slow relaxation to the room temperature was carried out over a period of 2 hours.

Then, a three-stage heat treatment was performed to form crystal phases. In a first crystallization step, the blanks were held at a temperature of 530° C. for 30 minutes. In a second step, they were heated to 670° C. and held at this temperature for almost 120 minutes. In a third step, the blanks were held at 800° C. for 30 minutes. This was followed by cooling to room temperature. Analysis showed that lithium disilicate is contained as the main crystal phase in the blanks. The crystal phase is in a ratio of approximately 1:1 to the glass content in percentage by volume. The size of the crystals/crystallites in the glass ceramic was a maximum of 2 μm.

A crown was then prepared chairside. For this purpose, a tooth preparation of a patient was scanned and the dental restoration was then milled from the blank using a CAD/CAM method. The dental restoration was then fitted and adapted. The crown was then removed to bring about smoothing to the gloss and healing of the damaged surface according to the teaching of the invention.

For this purpose, the dental restoration was exposed to infrared radiation emitted by quartz radiators, with the radiation component in the wavelength range between 2.5 and 4.7 μm being approximately 40%. As shown if FIG. 1, elongated quartz radiators 10, 12, 14, 16 were used, which in section formed an eight, as can be seen from the single FIGURE. Corresponding radiators 10, 12, 14, 16 delimited a parallelepiped space 18, in which the crown 20 was positioned. The crown 20 was exposed to infrared radiation over a period of about 60 seconds. In this case, heating alone was carried out, which led exclusively to a melting of the surface. This heating of the surface alone resulted in remediation of the damaged surface and in particular the cracks therein. At the same time, a gloss effect was achieved.

Since only a surface melting took place, cooling was rapid, so that the crown 20 could be reused after just approximately 1 min. Previously, the inner surface of the crown 20 was roughened by etching. Finally the crown was positioned and cemented in place.

Thus, a chairside treatment could be carried out in a very short period of time.

According to the teachings of the invention, a lithium silicate glass ceramic with a glass content of between 30 and 65% by volume and crystallite sizes in the glass ceramic of up to 2 μm and irradiation with an infrared radiation of between 2.5 μm and 4 μm is softened on the surface so that surface cracks or other damage that result upon surface treatment, such as milling, are repaired. At the same time, a gloss surface is obtained.

The strength is increased in a very short time, as possible surface damage is cured.

The glaze application according to the prior art, which is time-consuming, and the subsequent firing process are not required.

Optionally, it is possible to increase the strength by replacing lithium ions with alkali metal ions of greater diameter during treatment with infrared radiation. For this purpose, in the areas in which a strength increase is to be achieved, the form body, such as a dental restoration, is to be coated with a corresponding paste containing the alkali metal ions.

Although the teaching according to the invention preferably applies to the field of dental technology, it is not restricted to that field, but rather applies to all applications in which molded parts are produced from lithium silicate glass ceramic, in particular also in other medical fields.

The invention claimed is:

1. A method for the production of a monolithic form body, comprising the steps of:
   providing a blank;
   producing the monolithic form body by pressing and/or machining the blank; and
   softening of the form body exclusively in the surface region by irradiating the monolithic form body with infrared radiation.

2. The method according to claim 1, wherein the monolithic form body is softened to a depth T of T≤100 μm.

3. The method according to claim 1, further comprising the step of irradiating the monolithic form body with an infrared radiation whose main radiation components lie in the wavelength range between 2.7 μm and 4.7 μm.

4. The method according to claim 1, wherein the blank is a blank of lithium silicate glass ceramic that includes lithium disilicate as the main crystal phase.

5. The method according to claim 1, further comprising the step of heat-treating the monolithic form body after the producing step for the formation of metasilicate and/or disilicate crystals as the main crystal phase.

6. The method according to claim 1, wherein the blank is a monolithic form body of lithium silicate glass ceramic of which the glass content is in a ratio of 20:65 to the crystal component in percentage by volume.

7. The method according to claim 1, wherein crystal/crystallite size is ≤2 μm.

8. The method according to claim 1, wherein the monolithic form body is a dental restoration, which is removed from the mouth of a patient, grinded and then irradiated with infrared radiation and finally reinserted.

9. The method according to claim 1, further comprising the step of irradiating the monolithic form body with the infrared radiation over a time t where 10 seconds≤t≤150 seconds.

10. The method according to claim 1, wherein the monolithic form body includes a lithium silicate glass ceramic having a starting composition that comprises:

| | |
|---|---|
| 54.0-62.0% | by weight of SiO2; |
| 5.0-6.0% | by weight of Nucleating agents; |
| 1.5-3.5% | by weight of Al2O3; |
| 13.0-16.0% | by weight of Li2O; |
| 0.6-1.8% | by weight of K2O; |
| 8.0-11.5% | by weight of ZrO2; |
| 0-6.0% | by weight of B2O3; |
| 0-1.9% | by weight of Na2O; |
| 0-8.0% | by weight of color pigments. |

11. The method according to claim 1, wherein the monolithic form body includes a lithium silicate glass ceramic having a starting composition that comprises:

| | |
|---|---|
| 57.0-60.0% | by weight of SiO2; |
| 5.2-5.6% | by weight of Nucleating agents; |
| 2.6-3.2% | by weight of Al2O3; |
| 13.5-15.0% | by weight of Li2O; |
| 0.8-1.4% | by weight of K2O; |
| 9.0-11.0% | by weight of ZrO2; |
| 0-5.0% | by weight of B2O3; |
| 0-1.5% | by weight of Na2O; |
| 2-7.0% | by weight of color pigments; | and optionally CeO2.

12. The method according to claim 1, wherein the monolithic form body includes a lithium silicate glass ceramic having a starting composition that comprises:

| | |
|---|---|
| 58% | by weight of SiO2; |
| 5% | by weight of P2O5; |
| 3% | by weight of Al2O3; |
| 15% | by weight of Li2O; |
| 1% | by weight of K2O; |
| 10.0% | by weight of ZrO2; |
| 4% | by weight of color pigments; |
| 4% | by weight of additives. |

13. A method according to claim 1, further comprising the step of covering the monolithic form body, at least in sections, with a paste including alkali metal ions of greater diameter than lithium ions before subjected to its infrared irradiation.

14. The method according to claim 13, wherein the paste is applied to all the surfaces of the monolithic form body with a thickness D of 0.1 mm<D<0.4 mm.

15. The method according to claim 1, further comprising the step of coating the monolithic form body with a viscous solution or dispersion of a salt including an alkali metal ion as a paste.

16. The method according to claim 15, wherein the paste if formed from a mixture of the salt with at least one substance selected from the group consisting of 1,4-butanediol, hexanetriol, and a mixture of the two substances.

17. The method according to claim 1, further comprising the step of applying a paste to the monolithic form body by spraying.

* * * * *